United States Patent [19]

Merchant et al.

[11] Patent Number: 5,560,355
[45] Date of Patent: Oct. 1, 1996

[54] MEDICAL SENSOR WITH AMPLITUDE INDEPENDENT OUTPUT

[75] Inventors: Adnan I. Merchant, Fremont; Michael Bernstein, San Ramon, both of Calif.

[73] Assignee: Nellcor Puritan Bennett Incorporated, Pleasanton, Calif.

[21] Appl. No.: 169,093

[22] Filed: Dec. 17, 1993

[51] Int. Cl.$^6$ ........................................................ A61B 5/00
[52] U.S. Cl. ........................ 128/633; 128/666; 356/41
[58] Field of Search ................................ 128/633–634, 128/664–6; 356/41

[56] References Cited

U.S. PATENT DOCUMENTS

| | | | |
|---|---|---|---|
| 4,384,773 | 5/1983 | Hambly | 354/29 |
| 4,468,562 | 8/1984 | Wicnienski et al. | 356/416 |
| 4,759,369 | 7/1988 | Taylor | 128/633 |
| 4,846,183 | 7/1989 | Martin | 128/633 |
| 4,930,506 | 6/1990 | Ullrich | 128/633 |
| 4,947,033 | 8/1990 | Kordts et al. | 250/214 R |

FOREIGN PATENT DOCUMENTS 9221281  12/1992  WIPO .................................... 128/633

*Primary Examiner*—Angela D. Sykes
*Assistant Examiner*—Robert L. Nasser, Jr.
*Attorney, Agent, or Firm*—Townsend and Townsend and Crew LLP

[57] ABSTRACT

The present invention provides a medical sensor for detecting a blood characteristic. The sensor includes a transducer for producing an analog signal related to the blood characteristic. The analog signal is converted into a transmission signal which is in amplitude-independent form for transmission to a remote analyzer. In one embodiment, a current-to-frequency converter converts a signal from a pulse oximeter sensor into a frequency signal which can be transmitted over a transmission line to a remote pulse oximeter.

2 Claims, 5 Drawing Sheets

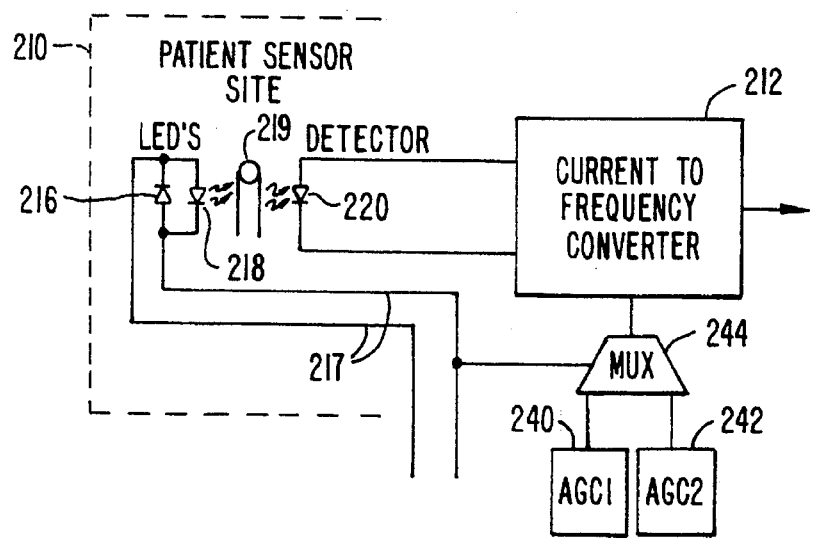
FIG. 2A.
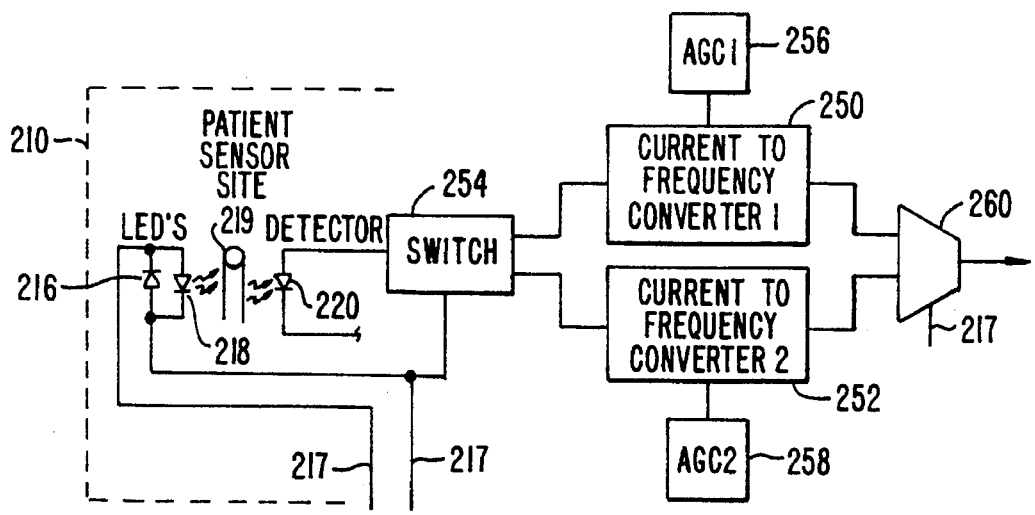
FIG. 2B.
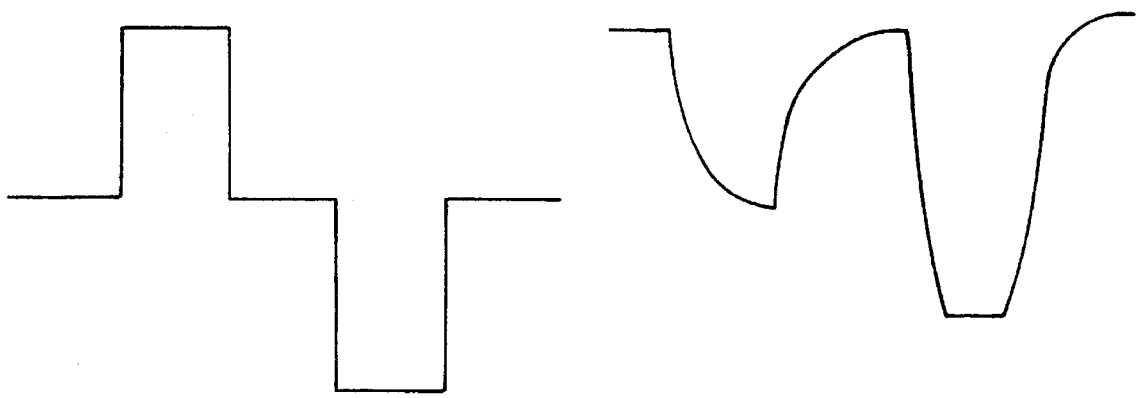
FIG. 3A.                    FIG. 3B.

MEDICAL SENSOR WITH AMPLITUDE INDEPENDENT OUTPUT

BACKGROUND OF THE INVENTION

The present invention relates to medical sensors, and in particular to the signals generated for transmission by such sensors.

Non-invasive photoelectric pulse oximetry is an example of a medical sensor which is well known and is described, for instance, in U.S. Pat. No. 4,911,167, incorporated herein by reference. Pulse oximeters typically measure blood flow characteristics including, but not limited to, blood oxygen saturation of hemoglobin in arterial blood. Pulse oximeters pulse light through body tissue where blood perfuses the tissue and photoelectrically sense the absorption of light in the tissue. The amount of light absorbed is used to calculate the amount of the blood constituent being measured.

FIGS. 1A and 1B together are a block diagram of an oximeter 100 such as the pulse oximeter model N-200 which is commercially available from Nellcor Incorporated, Hayward, Calif., U.S.A. FIG. 1A shows the sensor, patient module and analog front end of the oximeter. A patient sensor 110, for sensing and transmitting the pulsed light, includes a photodetector 112 and a pair of light emitting diodes 114, 116 ("LED's"). Typically, a first LED 114 emits light having a mean wavelength of about 660 nanometers in the red light range and the second LED 116 emits light having a mean wavelength of about 905 nanometers in the infrared range.

The photodetector 112 detects the red and infrared incident light, producing a current which changes value in response to the changes in the intensity of red and infrared light transmitted in sequence. The photodetector current produced has a small magnitude, typically in the range of $1 \times 10^{-9}$ amps. Because the current generated by the photodetector is so small, the signal is susceptible to inaccuracies caused by noise. In addition, the low current value generated decreases the degree of precision to which the detected signal can be accurately measured. By amplifying the photodetector current, noise susceptibility is decreased and the degree of precision to which the signal may be accurately measured is improved.

The detected current is converted to a voltage signal 122 and amplified by a combined current-to-voltage converter and amplifier 118 in a patient module 124, which may be separate from sensor 110. The sensor signal on line 122 from amplifier 118 is provided to an analog front-end circuit 120 which receives the amplified analog optical signal on line 122 from the patient module 124 and filters and processes it. The front-end circuit 120 separates the detected signal into red and infrared analog voltage signals 126, 128 corresponding to the detected red and infrared optical pulses. The voltage signal on line 122 is first passed through low pass filter 130 to remove unwanted high frequency components and AC coupled through capacitor 132 to remove the DC component and unwanted low frequency components. The signal is then passed through a buffer amplifier 134 to remove any unwanted low frequencies and a programmable gain stage 136 to amplify and optimize the signal level presented to the synchronous detector 138.

Synchronous detector 138 produces a synchronously-rectified voltage signal, and includes a two channel gating circuit which separates the signal into 2 components, one on line 140 representing the red light transmission and the other on line 142 representing the infrared light transmission. The separated signals on lines 140, 142 are filtered to remove the strobing frequency, electrical noise, and ambient noise and then digitized by an analog-to-digital converter ("ADC") section 144 (FIG. 1B). The digitized signal 146 is used by the microprocessor 148 to calculate the blood oxygen saturation.

It is well known that oxygen saturation may be computed to a useful accuracy by the formula:

$$\text{oxygen saturation} = AR^2 + BR + C \text{ where: } R = \frac{AC_R/AC_{IR}}{DC_R/DC_{IR}}$$

where $AC_R$ and $DC_R$ are respectively the AC and DC components of the red transmissivity signal, $AC_{IR}$ and $DC_{IR}$ are the AC and DC components of the infrared transmissivity signal, and A, B and C are constants determined by empirical curve fitting against the results of standard blood oxygen measurements. Because the AC and DC components of the red and infrared signals correspond to the maximum and minimum amplitude values of the detected signal, the measured AC and DC signals are critical in calculating the blood oxygen saturation of hemoglobin in arterial blood. The microprocessor 148 uses the maximum and minimum voltages received from the ADC 144 to calculate the blood oxygen saturation level.

Although amplification of the detected current improves the accuracy of the oxygen saturation calculation, the added circuitry necessary for amplification increases system cost, power dissipation and the number of possible sources of errors. The embodiment shown in FIG. 1 includes amplifiers 118, 134, 126, 128 to amplify the detected signal.

An alternative method and apparatus for measuring blood oxygen saturation which does not require amplification circuitry is needed.

SUMMARY OF THE INVENTION

The present invention provides a medical sensor for detecting a blood characteristic. The sensor includes a transducer for producing an analog signal related to the blood characteristic. The analog signal is converted into a transmission signal which is in amplitude-independent form for transmission to a remote analyzer. The signal is amplitude-independent because the information content of the signal is not affected by changes in signal amplitude. Examples of amplitude independent signals are frequency modulated waveforms and digital pulse trains. In one embodiment of the invention, a current-to-frequency converter converts a signal from a pulse oximeter sensor into a variable-frequency signal which can be transmitted over a transmission line to a remote pulse oximeter.

The transducer and converting means can be integrated onto a single semiconductor chip which can be mounted adjacent to or in the sensor itself. In one embodiment, an automatic gain control (AGC) circuit is connected to the current-to-frequency converter to set the nominal operating frequency of the current-to-frequency converter. Where the sensor is a light detector, a light-to-frequency converter can be used.

Other amplitude independent forms of the signal can be used instead of the frequency-modulated waveform produced by the current-to-frequency converter. A pulse-width modulated signal could be used. Any number of digital transmission techniques can be used, for another example. An advantage of the frequency or digital communication is that it is not amplitude dependent, and is thus relatively noise immune. Thus, the need for a preamplifier next to the sensor, or coaxial cable, can be eliminated. In addition, conversion circuitry in the remote analyzer (such as the pulse oximeter) can be eliminated since the frequency or digital signal could be used directly.

In one embodiment, the converting means, such as a current-to-frequency converter, could be in the remote analyzer itself. This would provide the cost savings advantage of eliminating some circuitry, although not the noise immunity during the transmission to the analyzer.

A further understanding of the nature and advantages of the present invention may be realized by reference to the remaining portions of the specification and the drawings.

BRIEF DESCRIPTION OF THE DRAWINGS

FIG. 2A is a block diagram of an alternate embodiment of the oximeter of FIG. 2 using two AGC circuits; shown.

FIG. 2B is a block diagram of a second alternate embodiment of the oximeter of FIG. 2 using two channels with two current-to-frequency converters;

FIG. 3A is a graphical representation of the pulse train generated by the red and infrared LEDs of the oximeter shown in FIGS. 1A and 1B;

FIG. 3B is a graphical representation of the output signal of the combined amplifier and current-to-voltage converter of the oximeter shown in FIGS. 1A and 1B;

DETAILED DESCRIPTION OF PREFERRED EMBODIMENT

Figure 2:
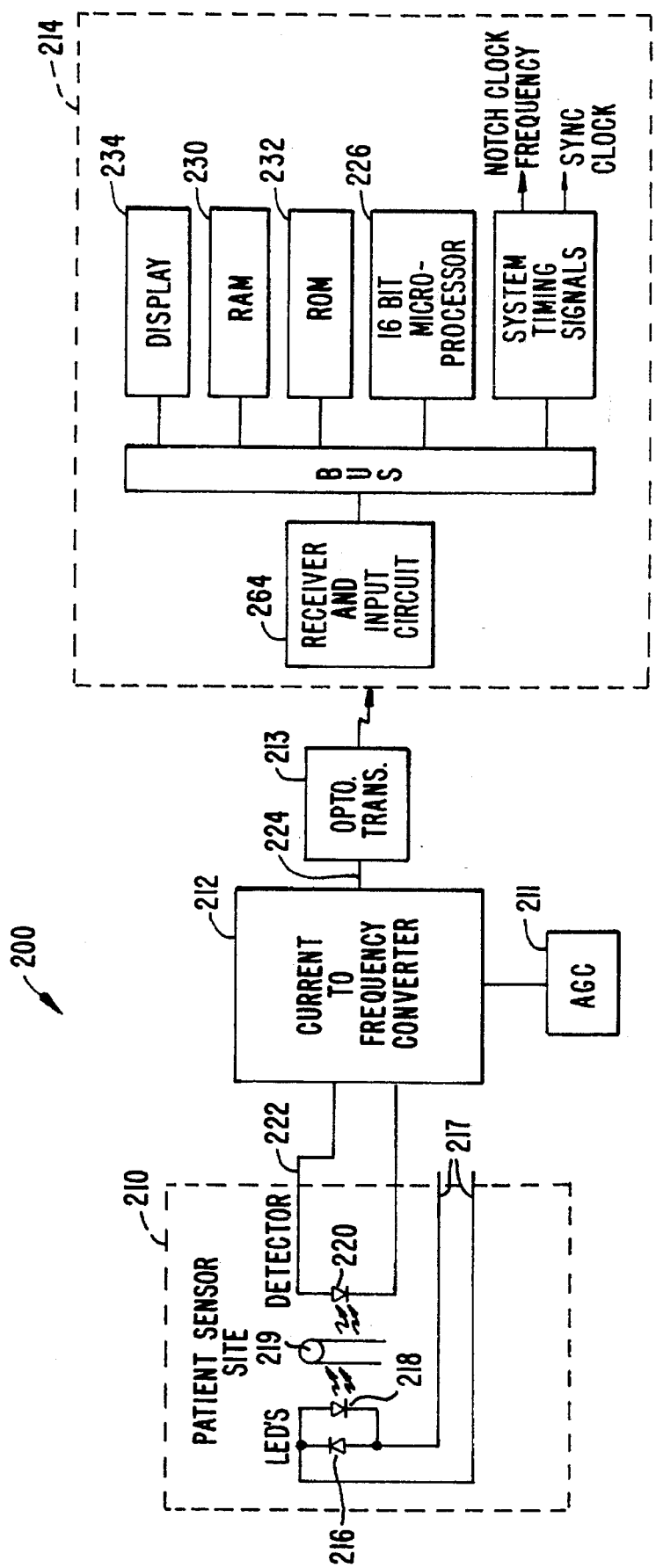
FIG. 2 shows a block diagram of an integrated pulse oximeter front-end according to the present invention.

FIG. 2 shows an embodiment of the present invention having a sensor 210, an automatic gain control (AGC) circuit 211, a current-to-frequency converter 212 and a signal processing unit 214. Sensor 210 includes a pair of LEDs 216, 218 and a photodetector 220.

The two LEDs 216, 218 have two different mean wavelengths: one having a mean wavelength of about 660 nanometers in the red light range, and the other having a mean wavelength of about 905 nanometers in the infrared range. A bipolar drive current to the two LEDs is provided on lines 217 by circuitry not shown. Alternate embodiments with more than two wavelengths or more than one detector are possible.

Typically the photodetector 220 is a photodiode. The photodiode 220 detects the level of light transmitted through the patient's tissue and produces an output current signal on a line 222 representing detected components of both the red and infrared light.

The photodetector output signal 222 is input into a current-to-frequency converter 212. An optional AGC circuit 211 is connected to converter 212. Current-to-frequency converters are well known in the art. The current-to-frequency converter 212 converts the photodetector output signal 222 into a signal on a line 224 whose frequency varies with the intensity of light received by the photodetector 220. Typically, the frequency increases as the intensity of light received increases.

The output of current-to-frequency converter 212 may be transmitted by a wire to Signal processing unit 214. Alternately, an optical transmitter 213 may be used, with a receiver and input circuit 215 in processing unit 214 being provided to receive the transmitted optical signal. In yet another embodiment, an RF transmission could be used instead of the optical transmission. An advantage of the present invention is the ability to use the frequency or digital signal directly for modulation of a light (IR, for example) or RF transmission.

In many pulse oximeters, the computation includes a step in which each time-varying signal component is normalized by dividing it by some measure of the overall signal amplitude. For example, if the "AC" component of a signal is characterized by the difference between local maximum and minimum amplitudes, we may have, for the red wavelength, for example: red normalized amplitude=(max.–min.)/min., or (max.–min.) /(average of max. and min.). The automatic gain control circuit 211 is optimal for such a pulse oximeter the variation of the gain through the AGC circuit will have no effect on the ultimate result. The AGC can be controlled by a signal from the oximeter signal processor, which adjusts the nominal output frequency whenever the output of the current-to-frequency converter is out of the range of the oximeter signal processor 214.

Current-to-frequency converter 212, along with the AGC circuit 211 and the optional optical transmitter 213 could be placed in a patient module between the sensor 210 and the pulse oximeter signal processor 214. In an alternate embodiment, the current-to-frequency converter and associated circuits can be combined with the sensor in the sensor housing 210. In yet another embodiment, the current-to-frequency converter can be in the processing unit 214 itself. Although this last embodiment does not provide the noise immunity available in the other embodiments, it does provide a reduction of circuitry.

FIG. 2A shows an alternate embodiment using two AGC circuits 240, 242. This allows two different gain settings for the red and infrared wavelengths, respectively. The LED pulsing signal on line 217 is provided to a multiplexer or switch 244 which selects between the two AGC circuits depending on whether the red or IR LED is being pulsed. Alternately, a single AGC as in FIG. 2 could be used, with the pulsing signal on line 217 being used to switch the AGC between two different gain settings for red and IR. This embodiment is possible where the switching frequency allows enough time for the AGC to switch its gain level. The embodiment of FIG. 2 with a single AGC setting for both red and IR will work where the nominal frequency for both wavelengths is sufficiently in the center of the range for the oximeter signal processor.

FIG. 2B shows yet another embodiment using two separate channels with two separate current-to-frequency converters 250, 252. Each of the current-to-frequency converters is connected directly to the photodetector 220 through a switch 254. The switch is controlled by the LED pulsing signal on line 217. Each channel has its own AGC circuit, 256, 258. The outputs of the current-to-frequency converters are selected through another switch or multiplexer 260, which is also controlled by the LED pulsing signal on line 217. Thus, each channel can have its nominal frequency set by its own AGC, and can be selected at both the input and output at the time of the red or IR LED being pulsed.

Figure 1A:
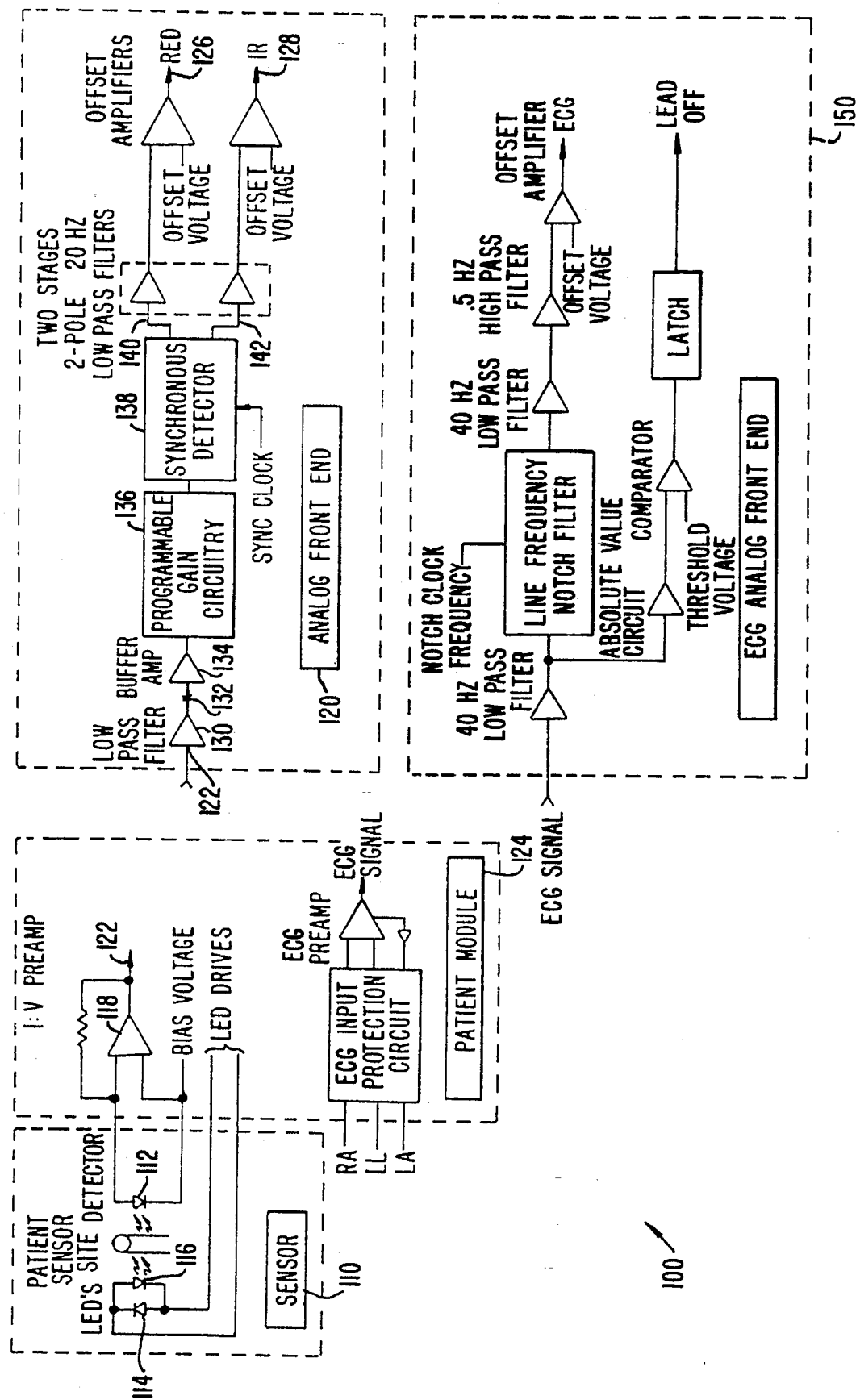
FIGS. 1A and 1B show a block diagram of a pulse oximeter front-end of the prior art.
Figure 1B:
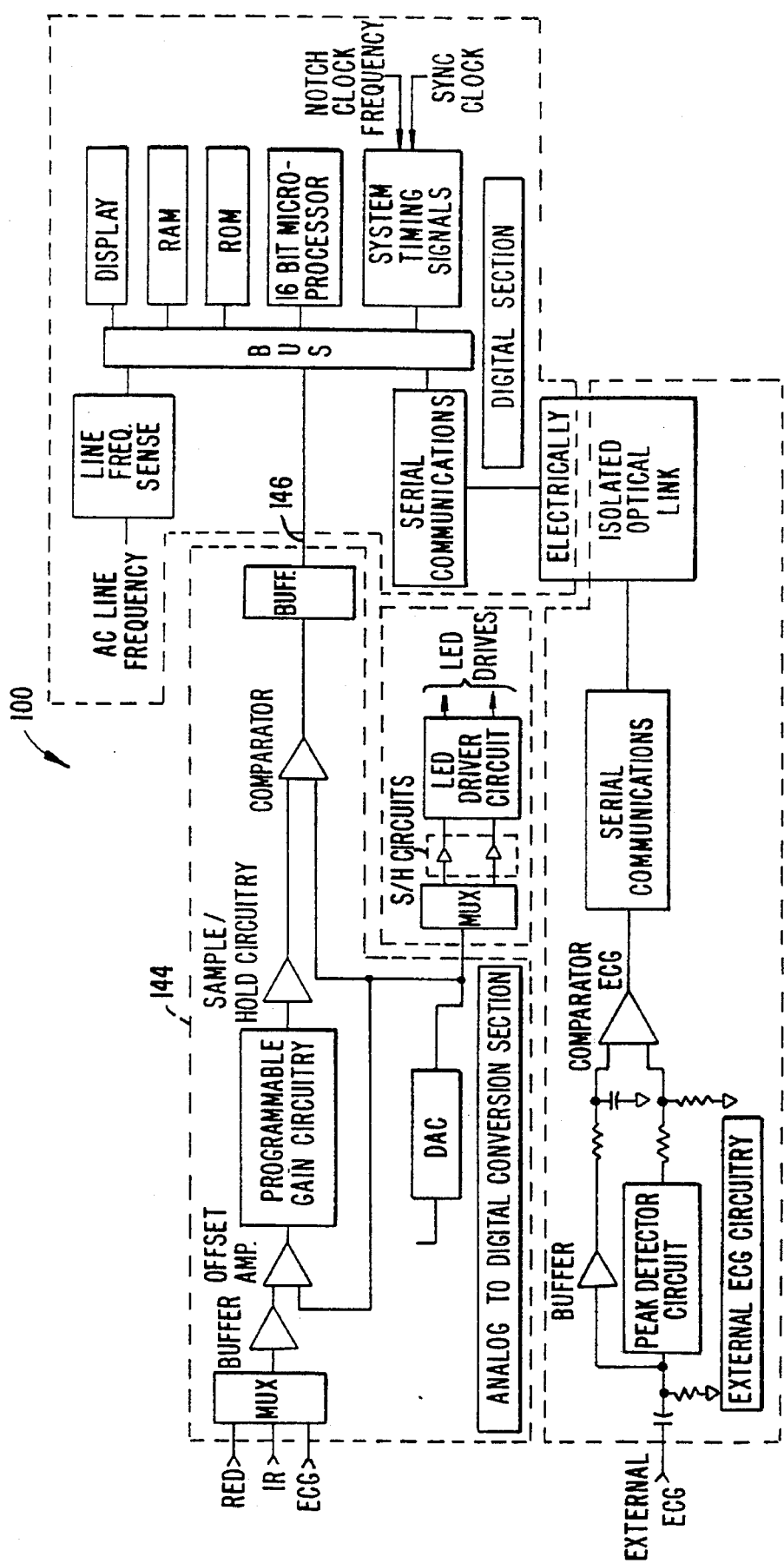
Figure 3C:
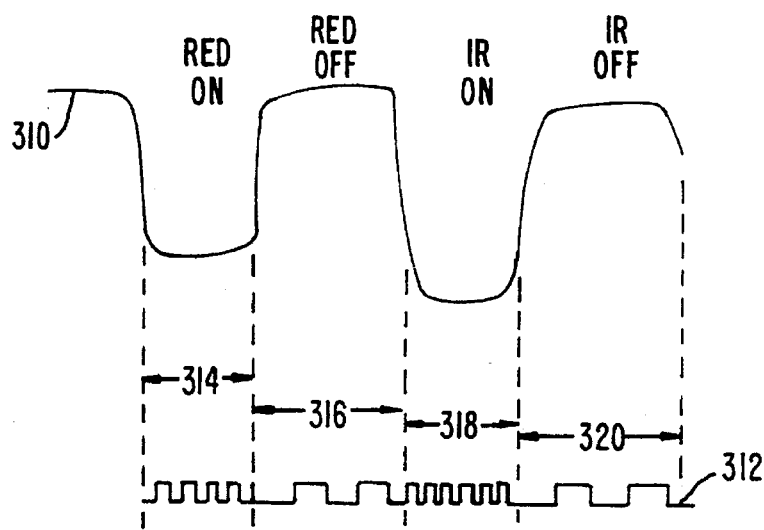
FIG. 3C is a graphical representation of the output signal from the current-to-frequency converter of the embodiment shown in FIG. 2.

FIGS. 3A and 3B show the pulse train driving the red and infrared LEDs 114, 116 (FIG. 3A) and the signal output 122 by the current-to-voltage converter 120 (FIG. 3B) for the oximeter system 100 shown in FIG. 1. FIG. 3D shows the prior art signal 310 from a current-to-voltage converter and the equivalent signal 312 on line 224 generated by the current-to-frequency converter 212 for the oximeter system 200 shown in FIG. 2. The frequency of signal 312 is a first value during a period 314 when the red LED is pulsed, and is a second, rest value when the red LED is off during a period 316. Similarly, a different frequency is transmitted during a period 318 when the IR LED is pulsed, and signal 312 returns to the rest frequency value during a period 320 when the IR LED is turned off.

Referring to FIG. 2, the frequency signal 224 produced by the current-to-frequency converter 212 produces a signal of sufficient magnitude for an accurate reading by the signal processing unit 214, with detection of just 2 states, the high and low levels, needed to convey information. Thus, the need for amplification of the photodetector output signal and the corresponding amplification, filtering and synchronization detection circuitry of FIG. 1 is eliminated. Thus implementation of the present invention does not require the current-to-voltage converter 118, the analog front-end circuit block 120, and the analog-to-digital conversion circuit block 144 needed for implementation of the prior art system shown in FIG. 1. Thus implementation of the present invention results in a reduction in circuitry compared to the prior art oximeter system 100. This reduction in circuitry decreases oximeter system costs, reduces power consumption, increases accuracy and results in a more compact and thus more mobile oximeter system.

Further, the amplification circuitry shown in the oximeter system illustrated in FIG. 1 may require a +/-15 volt power supply to drive the analog circuitry. Because the analog circuitry is eliminated by using the present invention, the 15 volt power supply may be replaced with a standard unipolar 5 volt power supply. Reduction of the voltage is important, since the decreased voltage results in a decrease in the power dissipation. Reduced power dissipation is particularly important in applications where the oximeter system relies on a battery for its source of power.

Preferably, a current-to-frequency converter which produces a pulse train output of varying frequency is used, rather than one with a sine wave output. Because the current-to-frequency converter output 224 is a digital signal, the signal on line 224 may be input directly into the signal processing unit 214. The signal processing unit 214 is typically comprised of a 32-bit microprocessor 226, and its associated support circuitry including a data bus 228, random access memory (RAM) 230, read only memory (ROM) 232, a conventional LED display device 234, and system timing circuit 236. In one preferred embodiment, the 32-bit microprocessor 226 is a model 80386, manufactured by Intel Corporation, Santa Clara, Calif.

The signal on line 224 fed into the signal processing unit 214 is typically in the range of 10 to 700 KHz. A normal digital input is read each clock period of the signal processing unit to determine its state. In order for the digital input to be read with a low error rate, the microprocessor 226 which drives the signal processing unit 214 operates at a frequency at least three to five times the rate of the current-to-frequency converter 212. However, typically the microprocessor 226 will operate in the 10 MHz to 30 MHz frequency range.

The input signal to signal processing unit 214 is first received by a receiver and input circuit 264. A receiver may be used where an optical transmitter 213 is used. The input signal will produce a count corresponding to the received signal, which is periodically sampled by microprocessor 226. In one embodiment, the input circuit 264 is a specialized digital signal processor chip. Such a configuration greatly increases the sophistication of signal analysis algorithms which can be implemented, because it frees most of the time of the processor 226 for performing such algorithms.

In the embodiment shown in FIG. 2, the synchronous detector is eliminated and the microprocessor separates the red and infrared signal based on the timing of pulsed signals. Since the drive current to the LEDs 216, 218 is provided by the signal processing unit 214, the microprocessor 226 knows the timing of the red and infrared signals produced by the LEDs, and therefore the timing of frequency signals produced in response to the red and infrared signals. Thus, since the microprocessor receives these frequency signals directly, there is no need to separate the detected red and infrared detected signals before providing an input to the microprocessor.

In an alternative embodiment, separation of the red and infrared frequency signals is not performed based on the microprocessor 226 generating the timing of alternating red and infrared frequency signals. Instead a digital I/O line is coupled from the LED drive lines to the microprocessor 226. Based on whether the I/O line input to the microprocessor 226 is high or low, the microprocessor knows if the frequency signal is generated by the red or infrared LED.

Figure 4:
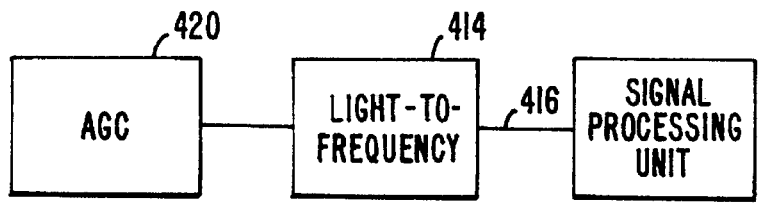
FIG. 4 is a block diagram of an alternate embodiment of an integrated pulse oximeter front-end of the present invention.

In an alternative embodiment shown in FIG. 4, both the photodetector and the current-to-frequency converter are replaced by a light-to-frequency converter 414, such as the Texas Instruments TSL220. The TSL220 device 414 combines a photodiode and current-to-frequency converter. The output voltage on line 416 of the light-to-frequency converter 414 is a pulse train whose frequency is directly proportional to the light intensity received by the light to frequency converter 414.

One benefit of using a light-to-frequency converter, such as the TSL220 device 414, is that the photodetector and current-to-frequency converter parts are combined and thus system cost is reduced. The output frequency range of the TSL220 may be varied by attaching an external capacitor or AGC circuit 420 to the light to frequency converter. If an external capacitor is used, its value is typically in the range of 0.1 to 100 nF. Embodiments such as shown in FIGS. 2A and 2B may be used, with multiple AGC circuits or multiple channels with multiple light-to-frequency converters.

Figure 5:
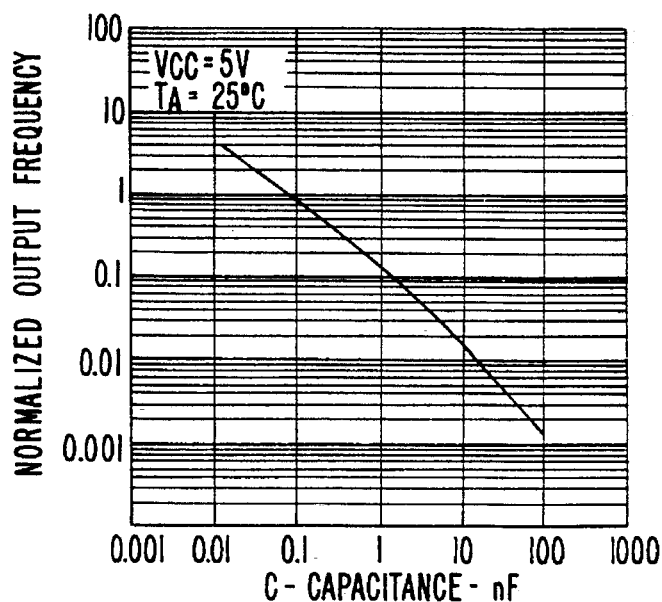
FIG. 5 is a graphical representation of the nominal output frequency versus capacitance for a current-to-frequency converter.

FIG. 5 shows a graphical representation of output frequency versus external capacitor value. Increasing the capacitance on the node decreases the output frequency. The capacitance value need not be precise to give a precise frequency, since it is the ratio of the frequencies, a normalized value, which is important (see discussion above with respect to FIG. 2).

Typically, the prior art patient module is separated from the photodetector sensor by a cable. Because of the capacitance added by the cable, it is desirable to keep the cable length to a minimum. The light-to-frequency converter 212 is necessarily included in the sensor. By adding light-to-frequency converter 212 the patient module is eliminated. The cable length to the oximeter may be correspondingly increased because the increased capacitance and noise associated with longer cable length does not significantly affect the pulse train frequency signal. Increasing the cable length between the sensor and the oximeter monitor is desirable because it increases patient mobility.

In some pulse oximeter systems, an ECG signal is available to correlate the heartbeat to the optical pulse such as described in U.S. Pat. No. 4,911,167. In an alternate embodiment of the present invention, the ECG signal is input into a voltage-to-frequency converter, so that the ECG is communicated as a frequency based signal. The frequency based ECG signal may be used according to the method described in U.S. Pat. No. 4,911,167. Similar to the frequency signal produced by the current-to-frequency converter, the frequency based ECG signal may not require the amplification circuitry found in the ECG analog front end 150.

As will be understood by those familiar with the art, the present invention may be embodied in other specific forms without departing from the spirit or essential characteristics thereof. For example, if a voltage signal is output from the photodetector, a voltage-to-frequency converter could be used in place of the current-to-frequency converter. Alternately, a time-interval encoded signal could be used instead of a frequency signal. The information could be conveyed by where a pulse is placed in a time slot, or the interval between signals could convey information. Accordingly, the disclosure of the preferred embodiment of the invention is intended to be illustrative, but not limiting, the scope of the invention which is set forth in the following claims.

What is claimed is:
1. A pulse oximeter system comprising:
(a) a sensor for attachment to a patient including
   a first light emitter for emitting light of a first wavelength,
   a second light emitter for emitting light of a second wavelength,
   a light to frequency converter integrated on a single semiconductor chip, said light to frequency converter including a photodetector and a current to frequency converter, and providing a frequency output signal,
   an automatic gain control circuit for separately adjusting the gain of said frequency output signal for said first and second wavelengths,
   a transmitter for transmitting said frequency output signal; and
(b) a pulse oximeter monitor including
   a receiver input for receiving said transmitted frequency output signal,
   a bus connected directly to said receiver input to receive said frequency output signal as a digital signal without any analog to digital conversion,
   a microprocessor, coupled to said bus, for analyzing said frequency output signal as a digital signal to determine a corresponding amplitude value represented by said frequency output signal, said microprocessor being programmed to measure oxygen saturation.
2. The pulse oximeter system of claim 1 wherein said transmitter is an electrical wire.

* * * * *